United States Patent
Takeyama et al.

(10) Patent No.: US 9,102,663 B2
(45) Date of Patent: Aug. 11, 2015

(54) METHOD FOR PRODUCING EPOXY COMPOUND HAVING CYANURIC ACID SKELETON

(75) Inventors: Toshiaki Takeyama, Funabashi (JP); Yuki Endo, Funabashi (JP); Sayoko Yanagisawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 124 days.

(21) Appl. No.: 13/814,015

(22) PCT Filed: Jul. 27, 2011

(86) PCT No.: PCT/JP2011/067112
§ 371 (c)(1),
(2), (4) Date: Mar. 13, 2013

(87) PCT Pub. No.: WO2012/017894
PCT Pub. Date: Feb. 9, 2012

(65) Prior Publication Data
US 2013/0172525 A1 Jul. 4, 2013

(30) Foreign Application Priority Data
Aug. 5, 2010 (JP) ................. 2010-176349

(51) Int. Cl.
| C08L 63/00 | (2006.01) |
| C08G 59/16 | (2006.01) |
| C07D 405/14 | (2006.01) |
| C08G 73/06 | (2006.01) |
| C08G 59/02 | (2006.01) |
| C08G 59/32 | (2006.01) |

(52) U.S. Cl.
CPC ............ C07D 405/14 (2013.01); C08G 59/027 (2013.01); C08G 59/3245 (2013.01); C08G 73/0644 (2013.01)

(58) Field of Classification Search
CPC .................................................. C07D 405/14
USPC ......................................... 525/523; 523/523
See application file for complete search history.

(56) References Cited

U.S. PATENT DOCUMENTS

| 2,537,816 A * | 1/1951 | Dudley ........................ 544/219 |
| 2,741,607 A | 4/1956 | Bradley et al. |
| 4,376,120 A | 3/1983 | Zeidler et al. |
| 2007/0295956 A1 | 12/2007 | Haitko |
| 2007/0295983 A1 | 12/2007 | Haitko |
| 2007/0299162 A1 | 12/2007 | Haitko |

FOREIGN PATENT DOCUMENTS

| JP | A-2010-1424 | 1/2010 |
| WO | WO 2006/035641 A1 | 4/2006 |
| WO | WO 2010/092947 A1 | 8/2010 |
| WO | WO 2011/093188 A1 | 8/2011 |
| WO | WO 2011/093236 A1 | 8/2011 |

OTHER PUBLICATIONS

Batog et al., "Cycloaliphatic epoxycyanurates for the preparation of polymers of increased thermal stability," *Chemical abstracts*, 1981, pp. 1549a - 1552a, vol. 95, Columbus, OH.
International Search Report issued in International Patent Application No. PCT/JP2011/067112 dated Sep. 20, 2011.
Jun. 5, 2014 Extended European Search Report issued in European Application No. 11814521.8.

* cited by examiner

*Primary Examiner* — Peter F Godenschwager
*Assistant Examiner* — David Karst
(74) *Attorney, Agent, or Firm* — Oliff PLC

(57) ABSTRACT

There is provided an epoxy compound that provides properties of cured products combining high transparency with high flexural strength by being thermally cured while maintaining advantageous handling properties in a liquid state thereof; and a method for producing a composition by using the epoxy compound. A method for producing an epoxy compound of Formula (1):

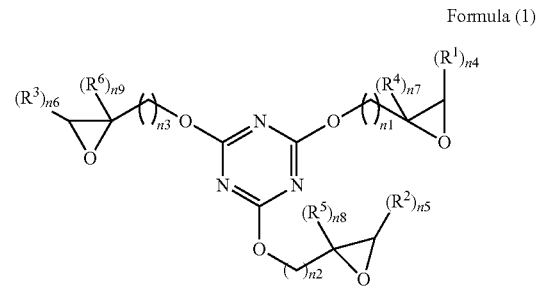

Formula (1)

(in Formula (1), n1, n2, and n3 are individually any one of integers of 2 to 6; n4, n5, and n6 are individually an integer of 2; n7, n8, and n9 are individually an integer of 1; and $R^1$, $R^2$, $R^3$, $R^4$, $R^5$, and $R^6$ are independently a hydrogen atom or a $C_{1-10}$ alkyl group), including: reacting cyanuric chloride with a $C_{4-8}$ alkenol and reacting the obtained compound having an unsaturated bond with a peroxide.

4 Claims, No Drawings

METHOD FOR PRODUCING EPOXY COMPOUND HAVING CYANURIC ACID SKELETON

TECHNICAL FIELD

The present invention relates to a method for producing a thermosetting epoxy compound. Furthermore, the present invention relates to a thermally polymerizable resin composition (a resin composition for electronic materials and optical materials) useful for obtaining a cured product having excellent characteristics such as high adhesion to a substrate, high transparency (transparency for a visible light ray), hard coating property, and high heat resistance, and a method for producing a cured product thereof (cured composite).

BACKGROUND ART

Conventionally, epoxy resins are widely used in the electronic material fields as an epoxy resin composition that combines an epoxy resin and a curing agent. Among the electronic material fields, for example, in the applications such as a high refractive-index layer of an antireflective film (an antireflective film for a liquid crystal display, and the like), an optical thin film (such as a reflecting plate), a sealant for electronic parts, a printed wiring substrate, and an interlayer insulation film material (such as an interlayer insulation film material for a built-up printed substrate), performances such as high adhesion to a base material, hard coating property, heat resistance, and high transparency for visible light are required for a molding material.

Crystalline epoxy resins generally have a rigid backbone skeleton and are multifunctional, so the crystalline epoxy resins have high heat resistance and are used in a field in which reliability for heat resistance is required such as the electric/electronic field.

In some fields, however, there is an application in which nothing but a liquid composition can be molded such as in casting molding. Thus, crystalline epoxy resins are limited to be used only in an application in which a solid material is used such as in transfer molding, and therefore, a range in which the crystalline epoxy resins can be used is limited.

Conventionally, epoxy resins used for liquid molding such as casting molding are liquid epoxy resins and cannot satisfactorily satisfy demand for enhancing properties of cured products such as heat resistance for which requirements have become increasingly severe recently in fields such as adhering, casting, sealing, molding, and laminating. Thus, demand for liquefying crystalline multifunctional epoxy resins providing a cured product having high heat resistance has increased. There is also demand for thermally curing the liquid epoxy resins.

An epoxy resin produced by esterifying a part of epoxy groups of a highly crystalline epoxy compound, for example, tris-(2,3-epoxypropyl)-isocyanurate, to lower the crystallinity so as to liquefy the highly crystalline epoxy compound has been disclosed (see Patent Document 1).

A compound in which an epoxy ring is bonded to a triazinetrione ring through a long chain alkylene group has been disclosed (see Patent Document 2).

An epoxy compound in which an epoxy ring is bonded to a triazinetrione ring through a long chain alkylene group and an epoxy resin composition using the epoxy compound have been disclosed (see Patent Documents 3, 4, and 5).

An epoxy compound in which an epoxy cyclohexyl group is bonded to a triazinetrione ring through an oxyalkylene group and an epoxy resin composition using the epoxy compound have been disclosed (see Patent Document 6).

An epoxy compound having a cyanuric acid skeleton that is produced by reacting cyanuric chloride and an epoxy alcohol, and a curable compound using the epoxy compound have been disclosed (see Patent Document 7).

RELATED-ART DOCUMENTS

Patent Documents

Patent Document 1: International Publication No. WO 2006/035641 pamphlet
Patent Document 2: U.S. Pat. No. 4,376,120 specification
Patent Document 3: US Patent No. 2007/0295956 specification
Patent Document 4: US Patent No. 2007/0295983 specification
Patent Document 5: US Patent No. 2007/0299162 specification
Patent Document 6: Japanese Patent Application Publication No. 2010-001424
Patent Document 7: U.S. Pat. No. 2,741,607 specification

SUMMARY OF THE INVENTION

Problem to be Solved by the Invention

In recent years, higher integration of circuits or the use of lead free solder has made the characteristics required for the epoxy resin cured product to be used even more severe particularly in the electric/electronic field. Therefore, with conventional liquid epoxy resins, the above characteristics have become difficult to be satisfied.

Because of their characteristics such as advantageous handling and fewer troubles in the production thereof such as an increase in viscosity due to crystallization, the liquid epoxy resins are used for potting, coating, and casting.

There has been increased demand for enlarging the application range of the crystalline epoxy resins by liquefying the crystalline epoxy resins, such as multifunctional epoxy resins, that provide a cured product having excellent physical properties such as high heat resistance.

There is also demand for performing curing of such epoxy resins by thermal curing.

The present invention provides: a method for producing an epoxy compound of which a thermally cured product has properties combining high transparency with high flexural strength while maintaining advantageous handling properties in a liquid state thereof for being used for a transparent sealant for an optical semiconductor, i.e., a transparent sealant for an LED (light emitting device); and a method for producing a curable composition containing the epoxy compound.

Means for Solving the Problem

The inventor of the present invention has found that by thermally curing an epoxy resin having a cyanuric acid skeleton with a curing agent such as an acid anhydride and an amine, a cured product or a cured coating film capable of compatibilizing excellent mechanical characteristics with excellent optical characteristics can be provided, and then, has completed the present invention.

The present invention is, according to a first aspect, a method for producing an epoxy compound of Formula (1):

Formula (1)

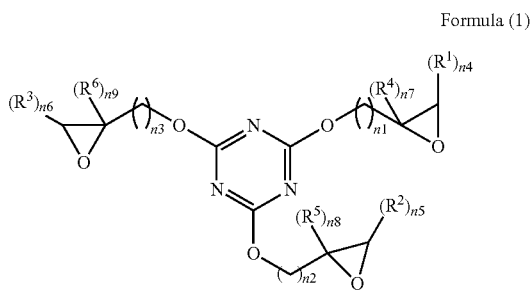

(in Formula (1), n1, n2, and n3 are individually any one of integers of 2 to 6; n4, n5, and n6 are individually an integer of 2; n7, n8, and n9 are individually an integer of 1; and $R^1$, $R^2$, $R^3$, $R^4$, $R^5$, and $R^6$ are independently a hydrogen atom or a $C_{1-10}$ alkyl group), the method characterized by including:

reacting cyanuric chloride with a $C_{4-8}$ alkenol and reacting the obtained compound having an unsaturated bond with a peroxide, according to a second aspect, the method according to the first aspect, in which the alkenol is 3-buten-1-ol, 4-penten-1-ol, 5-hexen-1-ol, 3-hexen-1-ol, or 3-methyl-3-buten-1-ol, according to a third aspect, the method according to the first aspect or the second aspect, in which the peroxide contains a peroxide structure or a percarboxylic acid structure, according to a fourth aspect, a method for producing a curable composition, characterized by including producing an epoxy compound of Formula (1) in accordance with the method described in any one of the first aspect to the third aspect and mixing the epoxy compound with a curing agent, according to a fifth aspect, the method according to the fourth aspect, in which the curing agent is an acid anhydride, an amine, a phenolic resin, a polyamide resin, imidazole, or a polymercaptan, and according to a sixth aspect, the method according to the fourth aspect or the fifth aspect, in which the curable composition contains the curing agent in a ratio of 0.5 to 1.5 equivalents relative to an epoxy group of the epoxy compound.

Effect of the Invention

With the method for producing the epoxy compound of the present invention, a side chain between the cyanuric acid moiety and the epoxy group is a long chain, so that the liquefaction of the obtained epoxy compound can be achieved. The curable composition of the present invention containing the epoxy compound has an enhanced completeness of the curing reaction of the epoxy group, so that the glass transition temperature of the cured product of the curable composition is stabilized and therefore, even in heated environment, the crosslinking density of the cured product is stabilized and toughness of the cured product can be maintained. In the curable composition of the present invention, the curing reaction of the epoxy group is completed in an initial stage of curing, so that the cured product of the curable composition of the present invention has stable flexural strength and stable elastic modulus.

Such effects are considered to be obtained because of the following reasons. That is, in a cured product of epoxy resin prepared by thermally curing a curable composition containing a compound in which an epoxy ring is bonded to cyanuric acid through a long chain alkylene group, the epoxy ring bonding through a long chain alkylene group has a large degree of freedom and high reactivity, so that all epoxy groups in the epoxy compound are involved in the reaction and the curable composition is converted into a cured product having high toughness.

In the present invention, a liquid epoxy compound having a long chain alkylene group is thermally cured using a curing agent such as an acid anhydride or an amine. The epoxy compound having a cyanuric acid skeleton obtained by the present invention has a low viscosity and high capacity of dissolving a curing agent. In addition, the cured product of the curable composition of the present invention has high toughness.

The epoxy compound used in the present invention has a low viscosity, so that the curable composition of the present invention has advantageous filling property.

MODES FOR CARRYING OUT THE INVENTION

The present invention is a method for producing an epoxy compound of Formula (1), characterized in that cyanuric chloride and a $C_{4-8}$ alkenol are reacted and the obtained compound having an unsaturated bond is reacted with a peroxide.

In Formula (1), n1, n2, and n3 are individually any one of integers of 2 to 6, preferably any one of integers of 2 to 4. n4, n5, and n6 are individually an integer of 2. n7, n8, and n9 are individually an integer of 1. $R^1$, $R^2$, $R^3$, $R^4$, $R^5$, and $R^6$ are independently a hydrogen atom or a $C_{1-10}$ alkyl group. $R^1$, $R^2$, $R^3$, $R^4$, $R^5$, and $R^6$ are independently a hydrogen atom or an organic group in which a hydrogen atom bonded to a carbon atom is substituted with an alkyl group.

Examples of the alkyl group include methyl, ethyl, n-propyl, isopropyl, cyclopropyl, n-butyl, isobutyl, sec-butyl, tert-butyl, cyclobutyl, 1-methyl-cyclopropyl, 2-methyl-cyclopropyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, cyclopentyl, 1-methyl-cyclobutyl, 2-methyl-cyclobutyl, 3-methyl-cyclobutyl, 1,2-dimethyl-cyclopropyl, 2,3-dimethyl-cyclopropyl, 1-ethyl-cyclopropyl, 2-ethyl-cyclopropyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, cyclohexyl, 1-methyl-cyclopentyl, 2-methyl-cyclopentyl, 3-methyl-cyclopentyl, 1-ethyl-cyclobutyl, 2-ethyl-cyclobutyl, 3-ethyl-cyclobutyl, 1,2-dimethyl-cyclobutyl, 1,3-dimethyl-cyclobutyl, 2,2-dimethyl-cyclobutyl, 2,3-dimethyl-cyclobutyl, 2,4-dimethyl-cyclobutyl, 3,3-dimethyl-cyclobutyl, 1-n-propyl-cyclopropyl, 2-n-propyl-cyclopropyl, 1-isopropyl-cyclopropyl, 2-isopropyl-cyclopropyl, 1,2,2-trimethyl-cyclopropyl, 1,2,3-trimethyl-cyclopropyl, 2,2,3-trimethyl-cyclopropyl, 1-ethyl-2-methyl-cyclopropyl, 2-ethyl-1-methyl-cyclopropyl, 2-ethyl-2-methyl-cyclopropyl, and 2-ethyl-3-methyl-cyclopropyl.

Examples of the alkenol include 3-buten-1-ol, 4-penten-1-ol, 5-hexen-1-ol, 3-hexen-1-ol, and 3-methyl-3-buten-1-ol. These alkenols are shown, for example, below.

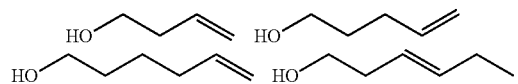

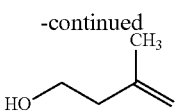

The compound having an unsaturated bond (intermediate) obtained by reacting cyanuric chloride and a $C_{4-8}$ alkenol is a compound of Formula (1-1):

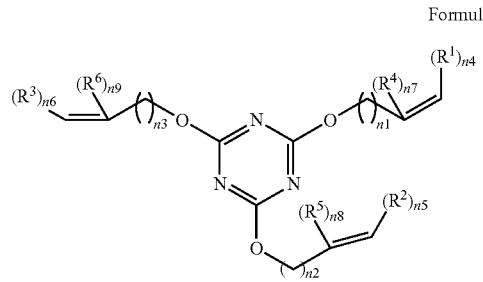

Formula (1-1)

(in Formula (1-1), n1, n2, and n3 are individually any one of integers of 2 to 6, preferably any one of integers of 2 to 4; n4, n5, and n6 are individually an integer of 2; n7, n8, and n9 are individually an integer of 1; and $R^1$, $R^2$, $R^3$, $R^4$, $R^5$, and $R^6$ are independently a hydrogen atom or a $C_{1-10}$ alkyl group).

In the method for producing an epoxy compound of the present invention, the method for producing the epoxy compound by reacting cyanuric chloride and n-pentan-1-en-5-ol, and oxidizing the obtained compound having an unsaturated bond and a peroxide, is shown below.

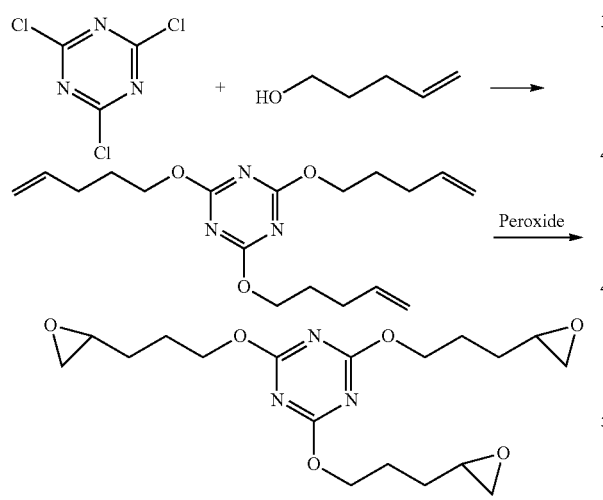

The reaction of cyanuric chloride and an alkenol is effected using a solvent such as tetrahydrofuran, dioxane, dimethylformamide, and toluene and using a base such as sodium hydride, sodium hydroxide, and potassium carbonate at a temperature of −20 to 100° C. for 1 to 12 hour(s). Then, by oxidizing the compound having an unsaturated bond with a peroxide, the epoxy compound can be obtained. Here, the peroxide is a peroxide containing a peroxy structure or a percarboxylic acid structure, and examples thereof include methachloroperbenzoic acid, peracetic acid, and hydrogen peroxide-tungstic acid. This reaction can be effected in a solvent such as methylene chloride, chloroform, and toluene at 0 to 110° C. for 1 to 10 hour(s).

The compound of Formula (1) obtained by the present invention is exemplified as follows.

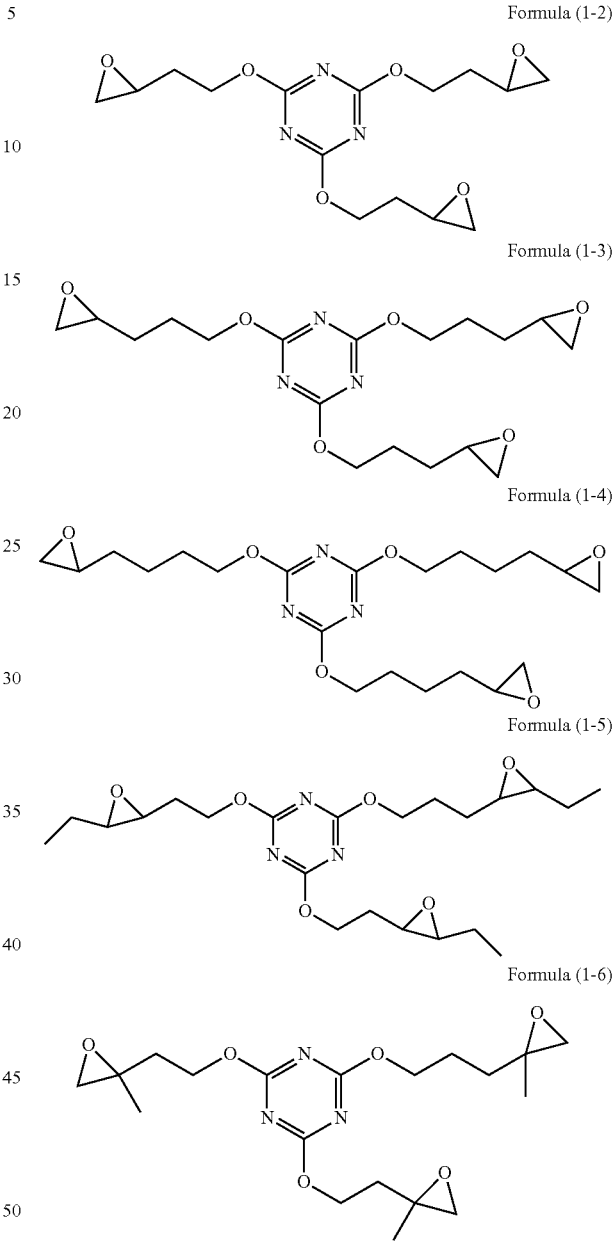

The present invention is a method for producing a curable composition, characterized in that the epoxy compound of Formula (1) is produced by the above method and the epoxy compound is mixed with a curing agent.

If necessary, the curable composition may further contain a solvent, another epoxy compound, a curing agent, a surfactant, and an adhesion accelerator.

The solid content of the curable composition in the present invention may be 1 to 100% by mass, 5 to 100% by mass, 50 to 100% by mass, or 80 to 100% by mass.

The solid content is a content of a component remaining after removing a solvent from the curable composition. In the present invention, a liquid epoxy compound is used and a curing agent is mixed with the liquid epoxy compound, so that, basically, a solvent is not necessary to be used, but if necessary, it is possible to add a solvent.

When the curing agent is an acid anhydride, an amine, a phenolic resin, a polyamide resin, imidazole, or a polymer-captan, the curing agent may be used in a ratio of 0.5 to 1.5 equivalents, preferably 0.8 to 1.2 equivalents, relative to the epoxy group. At this time, a curing assistant may be used in a ratio of 0.001 to 0.1 equivalents, relative to the epoxy group.

In the present invention, the epoxy compound of Formula (1) can be used in combination with another epoxy compound. The epoxy compound of Formula (1) and the other epoxy compound can be used in a molar ratio of the epoxy groups in a range of 1:0.1 to 1:0.5.

Examples of the other epoxy compound include compounds exemplified below.

Solid epoxy compound: tris-(2,3-epoxypropyl)-isocyanurate (of Formula (2-1), trade name: TEPIC, manufactured by Nissan Chemical Industries, Ltd.)

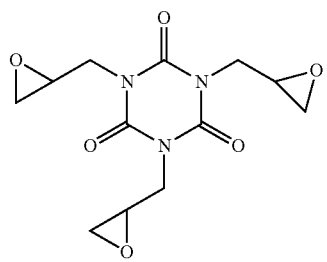

Formula (2-1)

Liquid epoxy compound: trade name: Epikote 828 (of Formula (2-2), manufactured by Japan Epoxy Resin Co., Ltd.)

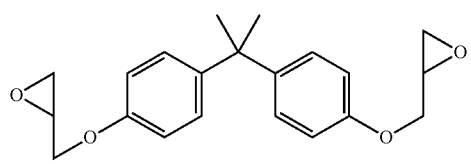

Formula (2-2)

Liquid epoxy compound: trade name: YX8000 (of Formula (2-3), manufactured by Japan Epoxy Resin Co., Ltd.)

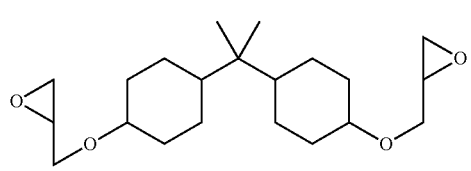

Formula (2-3)

Liquid epoxy compound: trade name: DME100 (of Formula (2-4), manufactured by New Japan Chemical Co., Ltd.)

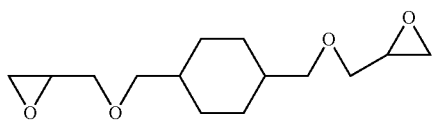

Formula (2-4)

Liquid epoxy compound: trade name: CE-2021P (of Formula (2-5), manufactured by Daicel Corporation)

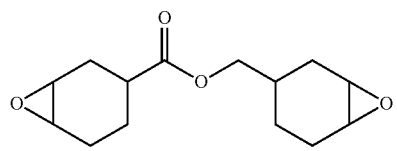

Formula (2-5)

As liquid epoxy compounds: tris-(3,4-epoxybutyl)-isocyanurate, tris-(4,5-epoxypentyl)-isocyanurate, and tris-(5,6-epoxyhexyl)-isocyanurate

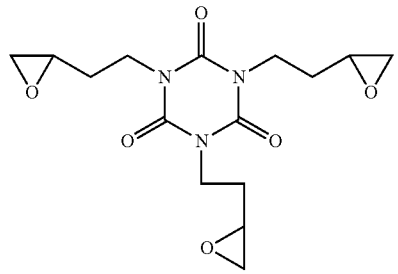

Formula (2-6)

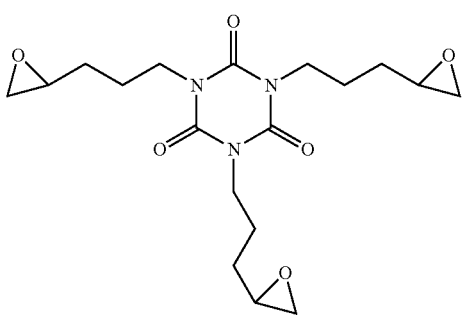

Formula (2-7)

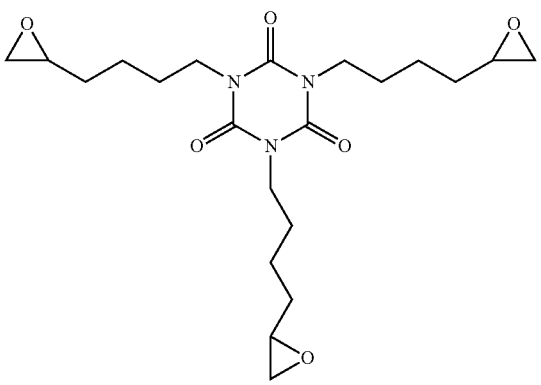

Formula (2-8)

Liquid epoxy compound: (of Formula (2-9), manufactured by Nissan Chemical Industries, Ltd., trade name: TEPIC-PAS B22) prepared by adding 0.8 mol of propionic anhydride to 1 mol of tris-(2,3-epoxypropyl)-isocyanurate to modify tris-(2,3-epoxypropyl)-isocyanurate. The compound of Formula (2-9) contains a compound of Formula (2-9-1), a compound of Formula (2-9-2), a compound of Formula (2-9-3), and a compound of Formula (2-9-4) in a molar ratio of (2-9-1):(2-9-2):(2-9-3):(2-9-4)=about 35%:45%:17%:3%.

Formula (2-9)

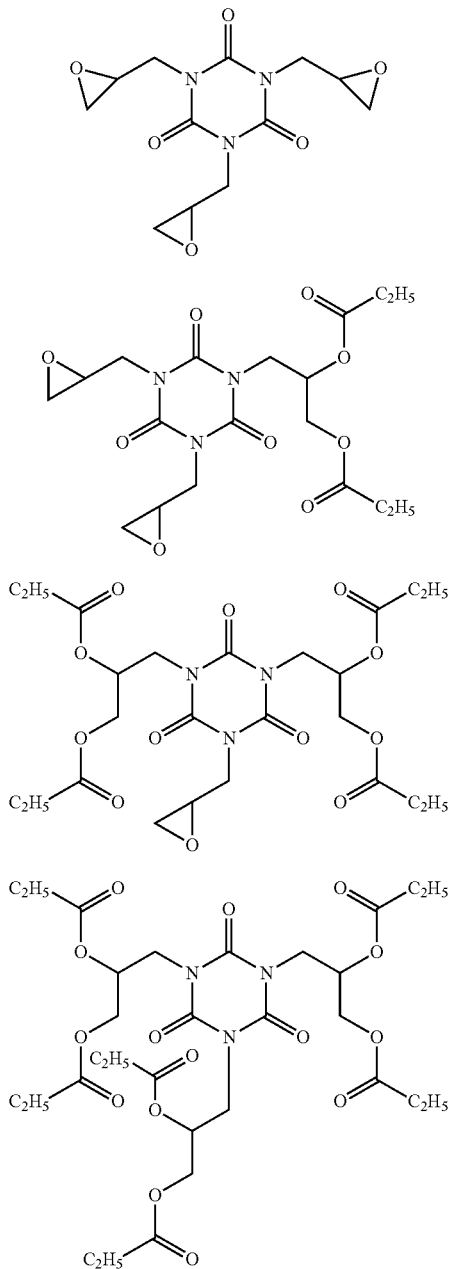

Liquid epoxy compound: (of Formula (2-10), manufactured by Nissan Chemical Industries, Ltd., trade name: TEPIC-PAS B26) prepared by adding 0.4 mol of propionic anhydride to 1 mol of tris-(2,3-epoxypropyl)-isocyanurate to modify tris-(2,3-epoxypropyl)-isocyanurate. The compound of Formula (2-10) contains a compound of Formula (2-10-1), a compound of Formula (2-10-2), and a compound of Formula (2-10-3) in a molar ratio of (2-10-1):(2-10-2):(2-10-3)=about 60%:32%:8%.

Formula (2-10)

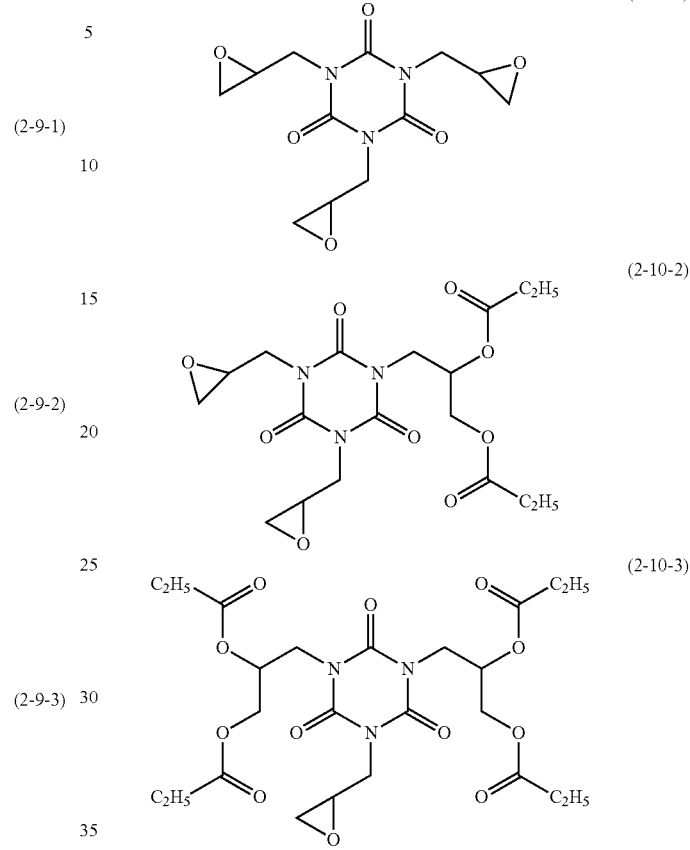

The equivalent of the curing agent relative to the epoxy compound is expressed in an equivalent ratio of the curable group of the curing agent relative to the epoxy group.

Examples of the curing agent include phenolic resins, amines, polyamide resins, imidazoles, polymercaptans, and acid anhydrides. Particularly, acid anhydrides and an amines are preferred.

A solid curing agent can be used as a solution prepared by dissolving the solid in a solvent. However, because the lowering of the density of the cured product or formation of pores caused by evaporation of the solvent lead to lowered strength and lowered water resistance of the cured product, the curing agent itself is preferably in a liquid state at normal temperature under normal pressure.

Examples of the phenolic resin include phenol novolac resins and cresol novolac resins.

Examples of the amines include piperidine, N,N-dimethylpiperazine, triethylenediamine, 2,4,6-tris(dimethylaminomethyl)phenol, benzyldimethylamine, 2-(dimethylaminomethyl)phenol, diethylenetriamine, triethylenetetramine, tetraethylenepentamine, diethylaminopropylamine, N-aminoethylpiperazine, di(1-methyl-2-aminocyclohexyl)methane, mencene diamine, isophorone diamine, diaminodicyclohexylmethane, 1,3-diaminomethylcyclohexane, xylenediamine, methaphenylenedimine, diaminodiphenylmethane, and diaminodiphenylsulfon. Among them, preferred to be used are diethylenetriamine, triethylenetetramine, tetraethylenepentamine, diethylaminopropylamine, N-aminoethylpiperazine, di(1-methyl-2-aminocyclohexyl)

methane, mencene diamine, isophorone diamine, and diaminodicyclohexylmethane that are in a liquid state.

Examples of the polyamide resins include a polyamideamine having in the molecule thereof, a primary amine and a secondary amine, which is generated by condensation of a dimer acid with a polyamine.

Examples of the imidazoles include 2-methylimidazole, 2-ethyl-4-methylimidazole, 1-cyanoethyl-2-undecylimidazolium trimellitate, and an epoxy imidazole adduct.

Examples of the polymercaptans include a polymercaptan in which a mercaptan group exists at a terminal of a polypropylene glycol chain and a polymercaptan in which a mercaptan group exists at a terminal of a polyethylene glycol chain, and among them, preferred are polymercaptans in a liquid state.

As the acid anhydrides as the curing agent, anhydrides of compounds having, in one molecule thereof, a plurality of carboxy groups is preferred. Examples of the acid anhydrides include phthalic anhydride, trimellitic anhydride, pyromellitic dianhydride, benzophenone tetracarboxylic anhydride, ethylene glycol bis-trimellitate, glycerol tris-trimellitate, maleic anhydride, tetrahydrophthalic anhydride, methyl tetrahydrophthalic anhydride, endo-methylene tetrahydrophthalic anhydride, methyl endo-methylene tetrahydrophthalic anhydride, methylbutenyl tetrahydrophthalic anhydride, dodecenylsuccinic anhydride, hexahydrophthalic anhydride, methyl hexahydrophthalic anhydride, succinic anhydride, methylcyclohexenedicarboxylic anhydride, and chlorendic anhydride.

Among them, preferred are methyl tetrahydrophthalic anhydride, methyl-5-norbornene-2,3-dicarboxylic anhydride (methylnadic anhydride or methylhimic anhydride), hydrogenated methylnadic anhydride, methylbutenyl tetrahydrophthalic anhydride, dodecenylsuccinic anhydride, methyl hexahydrophthalic anhydride, and a mixture of methyl hexahydrophthalic anhydride with hexahydrophthalic anhydride that are in a liquid state at normal temperature under normal pressure. The viscosity of these liquid acid anhydrides measured at 25° C. is around 10 mPas to 1,000 mPas.

When the above cured product is obtained, a curing assistant may be used, as appropriate, in combination with the curing agent. Examples of the curing assistants include: organic phosphorus compounds such as triphenylphosphine and tributylphosphine; quaternary phosphonium salts such as ethyltriphenylphosphonium bromide and tetrabutylphosphonium diethylphosphorodithioate; 1,8-diazabicyclo(5,4,0)undecane-7-ene; a salt of 1,8-diazabicyclo(5,4,0) undecane-7-ene with octylic acid; zinc octylate; and quaternary ammonium salts such as tetrabutylammonium bromide.

The content of the curing assistant may be 0.001 to 0.1 parts by mass, relative to 1 part by mass of the curing agent.

In the present invention, the epoxy compound of Formula (1) and the curing agent and if desired, the curing assistant are mixed to obtain the curable composition. The mixing can be performed using a reaction flask and a stirring propeller.

The mixing is performed, if necessary, by a heating-mixing method at a temperature of 10° C. to 100° C. for 0.5 to 1 hour.

The obtained liquid epoxy resin composition, that is, the curable composition of the present invention has a viscosity appropriate for being used as a liquid sealant. The liquid curable composition can be prepared to have any viscosity, and for being used as a transparent sealant for an LED or the like by a casting method, a potting method, a dispenser method, a printing method, or the like, the composition can perform partial sealing at any position. By mounting the liquid curable composition in a liquid state as it is by the above method directly on an LED or the like, and then, drying and curing the curable composition, an epoxy resin cured product can be obtained.

The curable composition is applied to a base material or is poured into a casting plate to which a mold releasing agent is applied, and by subjecting the curable composition to preliminary cure at a temperature of 100 to 120° C. and to postcure at a temperature of 120 to 200° C., a cured product can be obtained.

The curable composition of the present invention may contain a solvent. Examples of the solvent include: alcohols such as methanol and ethanol; ethers such as tetrahydrofuran; glycol ethers such as ethylene glycol monomethyl ether and ethylene glycol monoethyl ether; ethylene glycol alkyl ether acetates such as methylcellosolve acetate and ethylcellosolve acetate; diethylene glycols such as diethylene glycol monomethyl ether, diethylene glycol monoethyl ether, diethylene glycol dimethyl ether, diethylene glycol diethyl ether, and diethylene glycol ethyl methyl ether; propylene glycol monoalkyl ethers such as propylene glycol methyl ether, propylene glycol ethyl ether, propylene glycol propyl ether, and propylene glycol butyl ether; propylene glycol alkyl ether acetates such as propylene glycol methyl ether acetate, propylene glycol ethyl ether acetate, propylene glycol propyl ether acetate, and propylene glycol butyl ether acetate; propylene glycol alkyl ether acetates such as propylene glycol methyl ether propionate, propylene glycol ethyl ether propionate, propylene glycol propyl ether propionate, and propylene glycol butyl ether propionate; aromatic hydrocarbons such as toluene and xylene; ketones such as methyl ethyl ketone, cyclohexanone, and 4-hydroxy-4-methyl-2-pentanone; and esters such as methyl acetate, ethyl acetate, propyl acetate, butyl acetate, ethyl 2-hydroxypropionate, methyl 2-hydroxy-2-methylpropionate, ethyl 2-hydroxy-2-methylpropionate, methyl hydroxyacetate, ethyl hydroxyacetate, butyl hydroxyacetate, methyl lactate, ethyl lactate, propyl lactate, butyl lactate, methyl 3-hydroxypropionate, ethyl 3-hydroxypropionate, propyl 3-hydroxypropionate, butyl 3-hydroxypropionate, methyl 2-hydroxy-3-methylbutanate, methyl methoxyacetate, ethyl methoxyacetate, propyl methoxyacetate, butyl methoxyacetate, methyl ethoxyacetate, ethyl ethoxyacetate, propyl ethoxyacetate, butyl ethoxyacetate, methyl propoxyacetate, ethyl propoxyacetate, propyl propoxyacetate, butyl propoxyacetate, methyl butoxyacetate, ethyl butoxyacetate, propyl butoxyacetate, butyl butoxyacetate, methyl 2-methoxypropionate, ethyl 2-methoxypropionate, propyl 2-methoxypropionate, butyl 2-methoxypropionate, methyl 2-ethoxypropionate, ethyl 2-ethoxypropionate, propyl 2-ethoxypropionate, butyl 2-ethoxypropionate, methyl 2-butoxypropionate, ethyl 2-butoxypropionate, propyl 2-butoxypropionate, butyl 2-butoxypropionate, methyl 3-methoxypropionate, ethyl 3-methoxypropionate, propyl 3-methoxypropionate, butyl 3-methoxypropionate, methyl 3-ethoxypropionate, ethyl 3-ethoxypropionate, propyl 3-ethoxypropionate, butyl 3-ethoxypropionate, methyl 3-propoxypropionate, ethyl 3-propoxypropionate, propyl 3-propoxypropionate, butyl 3-propoxypropionate, methyl 3-butoxypropionate, ethyl 3-butoxypropionate, propyl 3-butoxypropionate, and butyl 3-butoxypropionate.

The thickness of the coated film can be selected from a range of around 0.01 μm to 10 mm depending on the application of the cured product.

As for the heating time, the heating can be performed for 1 to 12 hour(s), preferably around 2 to 5 hours.

EXAMPLE

Example 1

To 10.5 g of sodium hydride (purity: 60% or more), 200 mL of tetrahydrofuran was added and the resultant reaction mixture was cooled down to 0° C., followed by dropping 22.58 g of 4-penten-1-ol into the reaction mixture at 4° C. or less to be added. After the completion of the dropping, the resultant reaction mixture was stirred at room temperature for 2 hours. Then, the reaction mixture was cooled down again to 0° C. and into the reaction mixture, 11.9 g of 2,4,6-trichloro-1,3,5-triazine dissolved in 85 mL of tetrahydrofuran was slowly dropped at 15° C. or less to be added. At room temperature, the reaction was effected over one night and to the reaction mixture, water was added, followed by extracting the resultant reaction mixture with ethyl acetate. The extract was washed with water and was dried over anhydrous sodium sulfate and from the extract, the solvent was distilled off to obtain 21.9 g of a crude product. The crude product was purified with a column (ethyl acetate:hexane=1:10) to obtain 13.15 g of 2,4,6-tri(4-pentene-1-oxy)-1,3,5-triazine which is the objective substance as a transparent oil. Yield: 60%, Purity: 99.2% (GC)

To 5.4 g of 2,4,6-tri(4-pentene-1-oxy)-1,3,5-triazine, 85 mL of chloroform was added and the resultant reaction mixture was cooled down to 0° C. To the reaction mixture, 9.0 g of methachloroperbenzoic acid (purity: about 77%) was added and while elevating gradually the temperature of the resultant reaction mixture from 0° C. to room temperature, the reaction was effected over one night. To the reaction mixture, a 10% sodium thiosulfate aqueous solution was added and the resultant reaction mixture was extracted. The extract was washed with a sodium bicarbonate aqueous solution twice, was washed with water, and was dried over anhydrous sodium sulfate and from the extract, the solvent was distilled off to obtain 9.7 g of a crude product. The crude product was purified with a column (ethyl acetate:hexane=1:1 to 4:1) to obtain 4.8 g of 2,4,6-tri(4,5-epoxypentyl-1-oxy)-1,3,5-triazine (corresponding to Formula (1-3)) which is the objective substance as a transparent oil. Yield: 77%, Purity: 98.9% (GC)

Example 2

To 16.6 g of sodium hydride (purity: 60% or more), 600 mL of tetrahydrofuran was added and the resultant reaction mixture was cooled down to 0° C., followed by dropping 40.1 g of 3-hexen-1-ol into the reaction mixture at 4° C. or less to be added. After the completion of the dropping, the resultant reaction mixture was stirred at room temperature for 3 hours. Then, the reaction mixture was cooled down again to 0° C. and into the reaction mixture, 18.4 g of 2,4,6-trichloro-1,3,5-triazine dissolved in 120 mL of tetrahydrofuran was slowly dropped at 15° C. or less to be added. At room temperature, the reaction was effected over one night and to the reaction mixture, water was added, followed by extracting the resultant reaction mixture with ethyl acetate. The extract was washed with water and was dried over anhydrous sodium sulfate and from the extract, the solvent was distilled off to obtain 33.1 g of a crude product. The crude product was purified with a column (ethyl acetate:hexane=1:10) to obtain 23.22 g of 2,4,6-tri(3-hexene-1-oxy)-1,3,5-triazine which is the objective substance as a transparent oil. Yield: 61%, Purity: 98.6% (GC)

To 22.5 g of 2,4,6-tri(3-hexene-1-oxy)-1,3,5-triazine, 300 mL of chloroform was added and the resultant reaction mixture was cooled down to 0° C. To the reaction mixture, 49.7 g of methachloroperbenzoic acid (purity: about 77%) was added and while elevating gradually the temperature of the resultant reaction mixture from 0° C. to room temperature, the reaction was effected over one night. To the reaction mixture, a 10% sodium thiosulfate aqueous solution was added and the resultant reaction mixture was extracted. The extract was washed with a sodium bicarbonate aqueous solution twice, was washed with water, and was dried over anhydrous sodium sulfate and from the extract, the solvent was distilled off to obtain 27.9 g of a crude product. The crude product was purified with a column (ethyl acetate:hexane=1:4) to obtain 18.6 g of 2,4,6-tri(3,4-epoxyhexyl-1-oxy)-1,3,5-triazine (corresponding to Formula (1-5)) which is the objective substance as a transparent oil. Yield: 71%, Purity: 96.8% (GC)

Example 3

To 16.6 g of sodium hydride (purity: 60% or more), 600 mL of tetrahydrofuran was added and the resultant reaction mixture was cooled down to 0° C., followed by dropping 34.5 g of 3-methyl-3-buten-1-ol into the reaction mixture at 4° C. or less to be added. After the completion of the dropping, the resultant reaction mixture was stirred at room temperature for 3 hours. Then, the reaction mixture was cooled down again to 0° C. and into the reaction mixture, 18.5 g of 2,4,6-trichloro-1,3,5-triazine dissolved in 110 mL of tetrahydrofuran was slowly dropped at 15° C. or less to be added. At room temperature, the reaction was effected over one night and to the reaction mixture, water was added, followed by extracting the resultant reaction mixture with ethyl acetate. The extract was washed with water and was dried over anhydrous sodium sulfate and from the extract, the solvent was distilled off to obtain 31.1 g of a crude product. The crude product was recrystallized (ethyl acetate:hexane=1:10) and the filtrate was purified with a column (ethyl acetate:hexane=1:4) to obtain 26.1 g of 2,4,6-tri(3-methyl-3-butene-1-oxy)-1,3,5-triazine which is the objective substance as a white solid. Yield: 76%, Purity: 97.0% (GC)

To 25.4 g of 2,4,6-tri(3-methyl-3-butene-1-oxy)-1,3,5-triazine, 340 mL of chloroform was added and the resultant reaction mixture was cooled down to 0° C. To the reaction mixture, 61.6 g of methachloroperbenzoic acid (purity: about 77%) was added and while elevating gradually the temperature of the resultant reaction mixture from 0° C. to room temperature, the reaction was effected over one night. To the reaction mixture, a 10% sodium thiosulfate aqueous solution was added and the resultant reaction mixture was extracted. The extract was washed with a sodium bicarbonate aqueous solution twice, was washed with water, and was dried over anhydrous sodium sulfate and from the extract, the solvent was distilled off to obtain 22.4 g of a crude product. The crude product was purified by recrystallization (ethyl acetate:hexane=3:1) to obtain 18.3 g of 2,4,6-tri(3-methyl-3,4-epoxybutyl-1-oxy)-1,3,5-triazine (corresponding to Formula (1-6)) which is the objective substance as a white solid. Yield: 63%, Purity: 100% (GC)

Example 4

To 10.33 g (epoxy value=7.79) of 2,4,6-tri(4,5-epoxypentyl-1-oxy)-1,3,5-triazine obtained in Example 1, 13.17 g of MH-700 (manufactured by New Japan Chemical Co., Ltd., the component thereof is prepared by mixing 4-methylhexahydrophthalic anhydride with hexahydrophthalic anhydride in a molar ratio of 70:30) as a curing agent was added and at room temperature, the resultant reaction mixture was stirred and was degassed under reduced pressure for 30 minutes. To the reaction mixture, 110 mg of HISHICOLIN PX-4ET (manufactured by Nippon Chemical Industrial Co., LTD., component: tetrabutylphosphonium diethylphosphorodithioate) as a curing assistant was added and the resultant reaction mixture was stirred and degassed again. The reaction mixture was poured in between glass plates (which were treated with a mold releasing agent SR-2410) between which a silicone rubber of 3 mm was sandwiched and the reaction mixture was cured under conditions of preliminary cure: at 100° C. for 2 hours and postcure: at 150° C. for 5 hours.

Flexural strength: 156.0 MPa, flexural modulus: 3009 MPa, deflection until break: 9.35 mm, Tg (TMA): 165° C., linear expansion coefficient (30 to 80° C.): 87.0 ppm/° C., transmittance (400 nm): 44.6%, boiled water absorption rate (100 hour): 2.8%.

Example 5

To 12.61 g (epoxy value=7.01) of 2,4,6-tri(3,4-epoxy-hexyl-1-oxy)-1,3,5-triazine obtained in Example 2, 14.46 g of MH-700 (manufactured by New Japan Chemical Co., Ltd.) as a curing agent was added and at room temperature, the reaction mixture was stirred and was degassed under reduced pressure for 30 minutes. To the reaction mixture, 120 mg of HISHICOLIN PX-4ET (manufactured by Nippon Chemical Industrial Co., LTD.) as a curing assistant was added and the resultant reaction mixture was stirred and degassed again. The reaction mixture was poured in between glass plates (which were treated with a mold releasing agent SR-2410) between which a silicone rubber of 3 mm was sandwiched and the reaction mixture was cured under conditions of preliminary cure: at 100° C. for 2 hours and postcure: at 150° C. for 5 hours.

Flexural strength: 104.8 MPa, flexural modulus: 3238 MPa, deflection until break: 4.38 mm, Tg (TMA): 188° C., linear expansion coefficient (30 to 80° C.): 90.1 ppm/° C., transmittance (400 nm): 41.3%, boiled water absorption rate (100 hour): 2.8%.

INDUSTRIAL APPLICABILITY

The curable composition using the epoxy compound of the present invention obtained as a compound of Formula (1) has a high strength and an excellent transmittance.

According to the present invention, a curable composition using an epoxy compound having properties combining high transparency with high flexural strength when thermally cured while maintaining advantageous handling properties in a liquid state thereof can be provided.

The curable material using the liquid epoxy compound of the present invention has characteristics such as a low viscosity, fast curing, transparency, and small shrinkage on curing and can be used for coating or adhering of electronic parts, optical parts, or precision machine parts. The curable material using the liquid epoxy compound of the present invention can be used for adhering of, for example: an optical element such as a lens of a cellular phone or a camera, a light-emitting diode (LED), and a semiconductor laser (LD); parts such as a liquid crystal panel, a biochip, and a lens or a prism of a camera; magnetic parts of a hard disc of a personal computer or the like; a pickup (a part capturing optical information reflected from a disc) of a CD or DVD player; a cone and a coil of a speaker; a magnet of a motor; a circuit substrate; electronic parts; and parts inside an engine of an automobile and the like.

The present invention is applicable to, for example, a body of an automobile or a motorcycle, a lens or a mirror of a head light, a plastic lens of glasses, a cellular phone, a game machine, an optical film, and an ID card as an application to a hard coating material for surface protection of an automobile body, a lamp or electric appliances, a building material, a plastic, and the like.

Furthermore, examples of the application of the present invention include application to cards such as a credit card and a membership card, application to a printing ink for a switch and a keyboard of electric appliances and OA equipment, and application to an ink for an inkjet printer for a CD, a DVD, and the like as an application to an ink material for printing on a metal such as aluminum and a plastic.

Examples of the application of the present invention also include application to a technology for producing a complicated three-dimensional object by curing, in combination with a three-dimensional CAD, a resin, application to a photo fabrication such as modeling of industrial products, and applications to coating of an optical fiber, adhering, optical waveguide, and thick film resist (for MEMS).

The invention claimed is:

1. A method for producing a curable composition, the method comprising:
   reacting cyanuric chloride with a $C_{4-8}$ alkenol to produce a compound having an unsaturated bond;
   then reacting the compound having an unsaturated bond with a peroxide to produce an epoxy compound; and
   then mixing the epoxy compound with an acid anhydride, an amine, a phenolic resin, a polyamide resin, imidazole, or a polymercaptan as a curing agent; the epoxy compound having a structure represented by Formula (1):

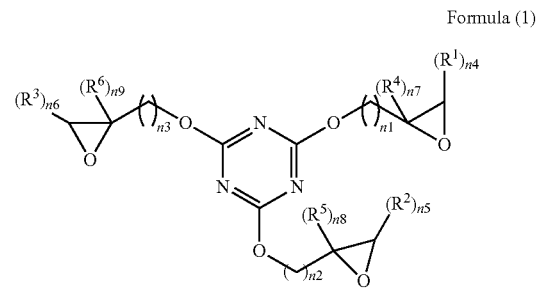

Formula (1)

where:
   each of n1, n2, and n3 is independently an integer in a range of from 2 to 6;
   each of n4, n5, and n6 is an integer of 2;
   each of n7, n8, and n9 is an integer of 1; and
   each of $R^1$, $R^2$, $R^3$, $R^4$, $R^5$, and $R^6$ is independently a hydrogen atom or a $C_{1-10}$ alkyl group.

2. The method according to claim 1, wherein the alkenol is 3-buten-1-ol, 4-penten-1-ol, 5-hexen-1-ol, 3-hexen-1-ol, or 3-methyl-3-buten-1-ol.

3. The method according to claim 1, wherein the peroxide contains a peroxide structure or a percarboxylic acid structure.

4. The method according to claim 1, wherein the curable composition contains the curing agent in a ratio in a range of from 0.5 to 1.5 equivalents relative to an epoxy group of the epoxy compound.

* * * * *